United States Patent
Senczuk et al.

(10) Patent No.: US 7,781,395 B2
(45) Date of Patent: Aug. 24, 2010

(54) PROCESS FOR PURIFYING PROTEINS

(75) Inventors: Anna Senczuk, Shoreline, WA (US); Ralph Klinke, Sammamish, WA (US)

(73) Assignee: Immunex Corporation, Thousand Oaks, CA (US)

( * ) Notice: Subject to any disclaimer, the term of this patent is extended or adjusted under 35 U.S.C. 154(b) by 229 days.

(21) Appl. No.: 10/895,581

(22) Filed: Jul. 21, 2004

(65) Prior Publication Data

US 2006/0229437 A1 Oct. 12, 2006

Related U.S. Application Data

(60) Provisional application No. 60/540,587, filed on Jan. 30, 2004.

(51) Int. Cl.
*C07K 16/00* (2006.01)

(52) U.S. Cl. .................................. 514/2; 530/387.1

(58) Field of Classification Search ............... None
See application file for complete search history.

(56) References Cited

U.S. PATENT DOCUMENTS

| 5,231,178 | A | * | 7/1993 | Holtz et al. | ............... 530/399 |
|---|---|---|---|---|---|
| 5,395,856 | A | | 3/1995 | Haase | |
| 5,928,915 | A | | 7/1999 | Warner et al. | |

* cited by examiner

*Primary Examiner*—Christopher R. Tate
*Assistant Examiner*—Roy Teller
(74) *Attorney, Agent, or Firm*—Christine M. Bellas

(57) ABSTRACT

The invention relates to a process for purifying a protein by mixing a protein preparation with a solution having a first salt and a second salt, wherein each salt has a different lyotropic value, and loading the mixture onto a hydrophobic interaction chromatography column. The dynamic capacity of the column for a protein using the two salt combination will be increased compared with the dynamic capacity of the column for either single salt alone.

13 Claims, 5 Drawing Sheets

PROCESS FOR PURIFYING PROTEINS

CROSS-REFERENCE TO RELATED APPLICATIONS

This application claims the benefit of U.S. provisional application No. 60/540,587, filed Jan. 30, 2004, the entire disclosure of which is relied on and incorporated by reference.

FIELD OF THE INVENTION

This invention relates to protein purification and specifically to a process for protein purification using hydrophobic interaction chromatography.

BACKGROUND OF THE INVENTION

The purification of proteins for the production of biological or pharmaceutical products from various source materials involves a number of procedures. Therapeutic proteins may be obtained from plasma or tissue extracts, for example, or may be produced by cell cultures using eukaryotic or procaryotic cells containing at least one recombinant plasmid encoding the desired protein. The engineered proteins are then either secreted into the surrounding media or into the perinuclear space, or made intracellularly and extracted from the cells. A number of well-known technologies are utilized for purifying desired proteins from their source material. Purification processes include procedures in which the protein of interest is separated from the source materials on the basis of solubility, ionic charge, molecular size, adsorption properties, and specific binding to other molecules. The procedures include gel filtration chromatography, ion-exchange chromatography, affinity chromatography, and hydrophobic interaction chromatography.

Hydrophobic interaction chromatography (HIC) is used to separate proteins on the basis of hydrophobic interactions between the hydrophobic moieties of the protein and insoluble, immobilized hydrophobic groups on the matrix. Generally, the protein preparation in a high salt buffer is loaded on the HIC column. The salt in the buffer interacts with water molecules to reduce the solvation of the proteins in solution, thereby exposing hydrophobic regions in the protein which are then adsorbed by hydrophobic groups on the matrix. The more hydrophobic the molecule, the less salt is needed to promote binding. Usually, a decreasing salt gradient is used to elute proteins from a column. As the ionic strength decreases, the exposure of the hydrophilic regions of the protein increases and proteins elute from the column in order of increasing hydrophobicity. See, for example, *Protein Purification*, 2d Ed., Springer-Verlag, New York, 176-179 (1988).

When developing processes for commercial production of therapeutically important proteins, increasing the efficiency of any intermediate purification steps is highly desirable. One way of improving the ease and efficiency of manufacturing is to increase the load capacity of one or more of the intermediate steps of the purification process to the point that the number of cycles required to purify a batch of protein is reduced without compromising the quality of the protein separation. The present invention improves the process of protein purification by increasing the capacity and efficiency of an intermediate step.

SUMMARY OF THE INVENTION

The present invention provides a process of purifying a protein comprising mixing a protein preparation with a solution containing a first salt and a second salt, forming a mixture which is loaded onto a hydrophobic interaction chromatography column, wherein the first and second salts have different lyotropic values, and at least one salt has a buffering capacity at a pH at which the protein is stable. In one embodiment, the pH of the mixture and equilibrium buffer is between about pH 5 and about pH 7. The process further comprises eluting the protein.

The present invention provides combinations of salts useful for increasing the dynamic capacity of an HIC column compared with the dynamic capacity of the column using separate salts alone. These combinations of salts allow for a decreased concentration of at least one of the salts to achieve a greater dynamic capacity, without compromising the quality of the protein separation. The first and second salt combinations are selected for each particular protein through a process of establishing precipitation curves for each salt individually, and precipitation curves for the combination of salts holding one salt constant and varying the second. The concentrations of the salt combinations can be optimized further, for example, to ensure protein stability at room temperature and to prevent formation of aggregates in the protein preparation.

Preferred first salts are those which form effective buffers at a pH at which the protein is stable. In one embodiment, the first and second salts are selected from acetate, citrate, phosphate, sulfate, or any mineral or organic acid salt thereof. In one embodiment the pH of the mixture is between about pH 5 and about pH 7. In one embodiment, the final salt concentrations of the first salt and second salts in the mixture are each between about 0.1M and 1.0 M, in another embodiment between about 0.3 M and about 0.7 M. The cations can be selected from any non-toxic cations, including $NH_4^+$, $K^+$, and $Na^+$. Preferred cations are those which do not tend to denature the protein or to cause precipitation in combination with other ions, including $NH_4^+$ and $Na^+$.

The two salt buffers of the present invention result in an increase in dynamic capacity of an HIC column for a particular protein compared with the dynamic capacity achieved by single salts. This results in decreased number of cycles required for purifying a batch of protein. Therefore, the present invention has special applicability to commercial manufacturing practices for making and purifying commercially important proteins.

BRIEF DESCRIPTION OF THE FIGURES

FIG. 1 shows dual salt precipitation curves for an antibody against EGFR performed as described in Example I below.

DETAILED DESCRIPTION OF THE INVENTION

Figure 1A:
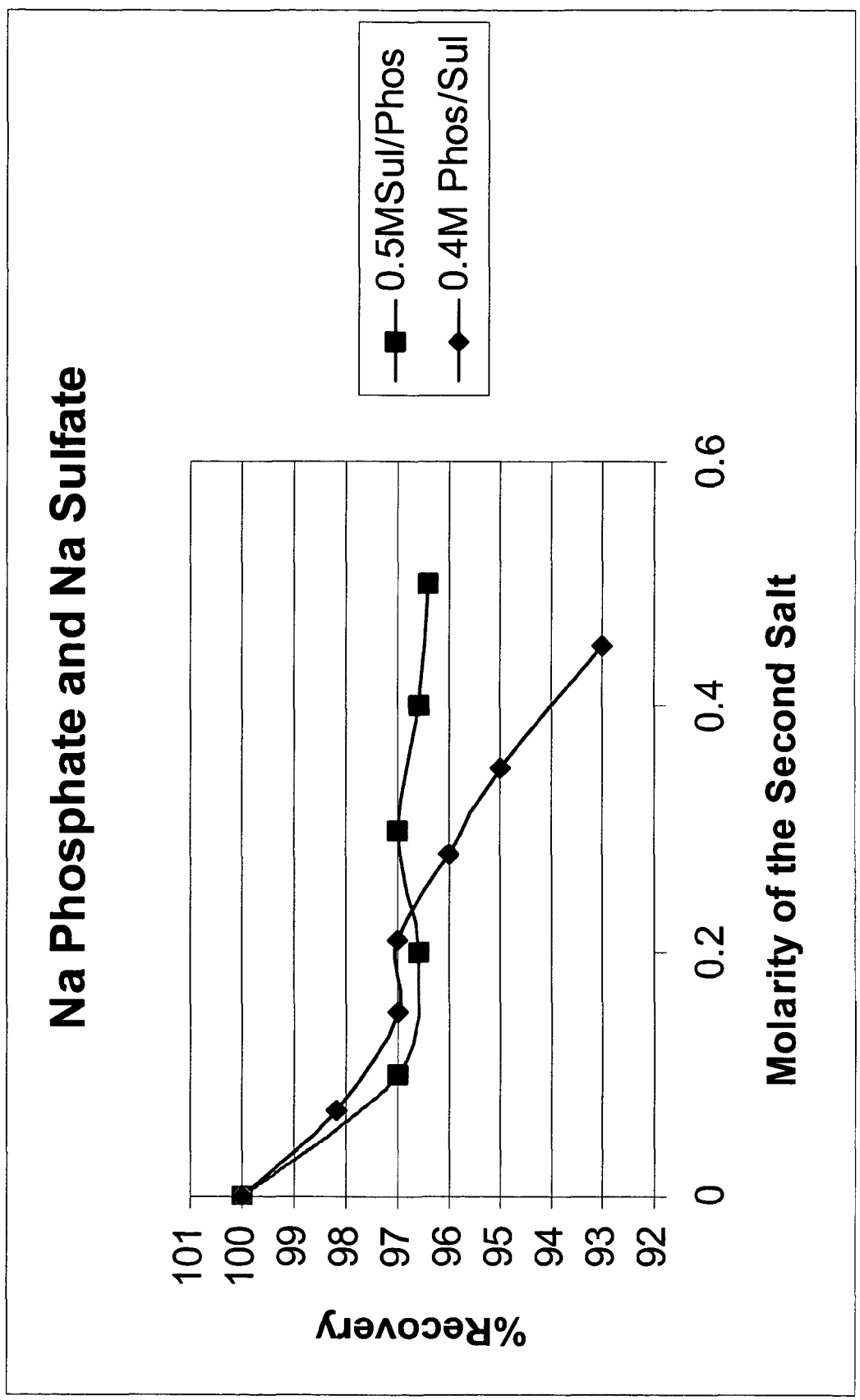
FIG. 1A shows the precipitation curve for 0.5 M sodium sulfate with increasing concentrations of sodium phosphate and the precipitation curve for 0.4 M sodium phosphate with increasing concentrations of sodium sulfate.

Hydrophobic interaction chromatography (HIC) is now widely used as an important bioseparation tool in the purification of many types of proteins. The process relies on separation of proteins on the basis of hydrophobic interactions between non-polar regions on the surface of proteins and insoluble, immobilized hydrophobic groups on the matrix. The absorption increases with high salt concentration in the mobile phase and the elution is achieved by decreasing the salt concentration of the eluant (Fausnaugh et al. *J Chromatogr* 359, 131-146 (1986)). A protein preparation at any stage of purification is "conditioned" in preparation for HIC by mixing with high salt buffers to prepare the HIC "load" to be loaded onto the column. Generally, salt conditions are adjusted to individual proteins. Generally, requirements of between about 0.7 and about 2 M ammonium sulfate and between about 1.0 and 4.0 M NaCl salt concentration has been considered as useful for purifying proteins using HIC columns. The practice was to add a high concentration of salt to a low concentration buffer solution, such as, for example, 1.4 M $NH_4SO_4$ added to a 0.024 M phosphate buffer for the purification of monoclonal antibodies at pH 7.2 (Nau et al. *BioChromotography* 62 (5), 62-74 (1990)); or 1.7 M ammonium sulfate in 50 mM $NaPO_4$ for purifying yeast cell surface proteins (Singleton et al., *J. Bacteriology* 183 (12) 3582-3588 (2001)). The present invention differs from these practices in the use of an intermediate concentration of a buffering salt in combination with an intermediate concentration of a second buffering salt, or in combination with an intermediate concentration of a second non-buffering salt, to achieve increased dynamic capacity.

It has also been recognized that increasing salt concentrations can increase the "dynamic capacity" of a column, or the amount of protein that can be loaded onto a column without "breakthrough" or loss of protein to the solution phase before elution. At the same time, high salt can be detrimental to protein stability. High salt increases the viscosity of a solution, results in increased formation of aggregates, results in protein loss due to dilution and filtration of the protein after elution from the column, and can lead to reduced purity (Queiroz et al., *J. Biotechnology* 87:143-159 (2001), Sofer et al., *Process Chromatography*, Academic Press (1999)). The present invention, however, provides a process of purifying proteins that increases the dynamic capacity of an HIC column for a particular protein while reducing the concentration of the salts used, without reducing the quality of the protein separation or raising manufacturing issues.

As used herein, the term "hydrophobic interaction chromatography (HIC)" column refers to a column containing a stationary phase or resin and a mobile or solution phase in which the hydrophobic interaction between a protein and hydrophobic groups on the matrix serves as the basis for separating a protein from impurities including fragments and aggregates of the subject protein, other proteins or protein fragments and other contaminants such as cell debris, or residual impurities from other purification steps. The stationary phase comprises a base matrix or support such as a cross-linked agarose, silica or synthetic copolymer material to which hydrophobic ligands are attached.

As used herein the term "dynamic capacity" of a separation column such as a hydrophobic interaction column refers to the maximum amount of protein in solution which can be loaded onto a column without significant breakthrough or leakage of the protein into the solution phase of a column before elution. More formally, K' (capacity factor)=moles of solute in stationary phase divided by moles of solute in mobile phase=Vr-Vo/Vo, where Vr is the volume of the retained solute and Vo is the volume of unretarded solute. Practically, dynamic capacity of a given HIC column is determined by measuring the amount of protein loaded onto the column, and determining the resin load which is mg protein/column volume (mg/ml-r). The amount of protein leaving the column in the solution phase after the column is loaded ("breakthrough") but before elution begins can then be measured by collecting fractions during the loading process and first wash with equilibrium buffer. The load at which no significant breakthrough occurs is the dynamic capacity of the protein for those conditions.

As used herein, the term "buffer" or "buffered solution" refers to solutions which resist changes in pH by the action of its conjugate acid-base range. Examples of buffers that control pH at ranges of about pH 5 to about pH 7 include citrate, phosphate, and acetate, and other mineral acid or organic acid buffers, and combinations of these. Salt cations include sodium, ammonium, and potassium. As used herein the term "loading buffer" or "equilibrium buffer" refers to the buffer containing the salt or salts which is mixed with the protein preparation for loading the protein preparation onto the HIC column. This buffer is also used to equilibrate the column before loading, and to wash to column after loading the protein. The "elution buffer" refers to the buffer used to elute the protein from the column. As used herein, the term "solution" refers to either a buffered or a non-buffered solution, including water.

As used herein, the term "lyotropic" refers to the influence of different salts on hydrophobic interactions, more specifically the degree to which an anion increases the salting out effect on proteins, or for cations, increases the salting-in effect on proteins according to the Hofmeister series for precipitation of proteins from aqueous solutions (Queiroz et al. *J. Biotechnology* 87: 143-159 (2001), Palman et al. *J. Chromatography* 131, 99-108 (1977), Roe et al. *Protein Purification Methods: A Practical Approach*. IRL Press Oxford, pp. 221-232 (1989)). The series for anions in order of decreasing salting-out effect is: $PO_4^{3-}$->$SO_4^{2-}$->$CH_3COO$->$Cl$->$Br$->$NO_3$->$ClO_4$->$I$->$SCN$-, while the series for cations in order of increasing salting-in effect: $NH_4+$<$Rb+$<$K+$<$Na+$<$Li+$<$Mg^2+$<$Ca^2+$<$Ba^2+$ (Queiroz et al., supra). According to the present invention, combining two different salts having different lyotrophic values with a protein preparation allows more protein to be loaded onto a column with no or negligible breakthrough compared with higher salt concentrations of each single salt.

It is an objective of the present invention to produce conditions for particular proteins which maximize the amount of protein which can be loaded and retained by an HIC column with little or no reduction in the quality of separation of the protein. The present invention is a process for purifying a protein comprising mixing a protein preparation with a buffered salt solution containing a first salt and a second salt, wherein each salt has a different lyotropic value, and loading the protein salt mixture onto an HIC column.

It is now understood that several factors influence the hydrophobic interactions which control the retention of a native protein to the hydrophobic groups attached to the matrix. These include van der Waals forces, or electrostatic interactions between induced or permanent dipoles; hydrogen bonding, or electrostatic interactions between acidic donor and basic acceptor groups; the hydrophobicity of the protein itself; and the influence of various salts on hydrophobic interactions. (Queiroz et al., *J Biotechnology* 87:143-159 (2001)). The Hofmeister ("lyotropic") series is an ordering of anions and cations in terms of their ability to precipitate proteins from aqueous solutions, as described above. The series for anions in order of decreasing salting-out effect is: $PO_4^{3-} \to SO_4^{2-} \to CH_3COO^- \to Cl^- \to Br^- \to NO_3^- \to ClO_4^- \to I^- \to SCN^-$, while the series for cations in order of increasing salting-in effect: $NH_4^+ < Rb^+ < K^+ < Na^+ < Li^+ < Mg^{2+} < Ca^{2+} < Ba^{2+}$ (Queiroz et al., supra)

The ions at the beginning of the series promote hydrophobic interactions and protein precipitation or salting out effects, and are called antichaotropic (Queiroz et al., supra). They are considered to be water structuring, whereas the ions at the end of the series are salting-in or chaotropic ions, and randomize the structure of water and tend to decrease the strength of hydrophobic interactions and result in denaturation (Porath et al., *Biotechnol Prog* 3: 14-21 (1987)). The tendency to promote hydrophobic interactions is the same tendency which promotes protein precipitation, and thus determining the salt concentration which causes a particular protein to begin to precipitate is a means of determining an appropriate concentration of that salt to use in an HIC column.

According to the present invention a first salt and a second salt are selected which have differing lyotropic values. This combination of salts acts together to increase the dynamic capacity of the HIC column for a particular protein. It has been found according to the present invention that each salt in combination can be provided at a lower concentration that the concentration of the salt alone to achieve a higher dynamic capacity for a protein compared with the dynamic capacity using a single salt. According to the present invention at least one salt has a buffering capacity at the desired pH.

According to the present invention, the appropriate concentrations of the salts are determined for a particular protein by generating precipitation curves for individual salts, then for combined salts. On the basis of individual salt precipitation curves, precipitation curves for combinations of salts are generated by holding one salt concentration constant, and varying the concentration of the second salt. Then the concentration of the second salt is held constant, and the concentration of the first salt is varied. From these two-salt precipitation curves, concentrations of salts useful for increasing the dynamic capacity of an HIC column can be determined. This is demonstrated in Examples 1 and 2 below, in which the concentrations of two salt combinations are determined using precipitation curves for each particular protein. In addition, the salt concentrations can be optimized to in order to confer additional stability on a protein at room temperature, for example, or to limit aggregate formation. Therefore, the present invention further provides a method of maximizing the dynamic capacity of a hydrophobic interaction chromatography column for a particular protein by selecting a combination of concentrations for a first and second salt having different lyotropic values by generating a series of precipitation curves for the salts alone, and then in combination holding a each salt constant while varying the second.

The salts of the present invention are selected from those having a buffering capacity at the pH at which the protein to be purified is stable. In one embodiment, salt combinations are chosen with a buffering capacity at between about pH 5 to about 7. These include, for example, citrate, phosphate, and acetate, and other mineral acid or organic acid buffers, and combinations of these. A second salt is selected from a salt which may or may not buffer at the desired pH, and can be added to the buffered solution, such as ammonium or sodium sulfate. Cations are selected from those which are non-toxic and non-denaturing. Preferred cations according to the present invention are sodium, potassium, and ammonium, with sodium being the most preferred for manufacturing purposes. Preferred salts for purifying proteins according to the present invention include combinations of sodium citrate, sodium phosphate, sodium acetate, and sodium sulfate.

The concentration of the salts used according to the present invention will depend on the characteristics of the particular salts. In one embodiment, the salts are used at concentrations from about 0.1 M to about 1.0 M in the final concentration of the mixture of salt solution and protein preparation depending on the salt and protein, in another embodiment is in the range between about 0.3 M and about 0.7 M. The pH of the buffered solution may be varied depending on requirements of the protein separation. In one embodiment, the pH varies between about pH 5 to about pH 7.

Hydrophobic Interaction Chromatography Column

The present invention can be used with any type of HIC stationary phase. Stationary phases vary in terms of ligand, ligand chain length, ligand density, and type of matrix or support. Ligands used for HIC include linear chain alkanes with and without an amino group, aromatic groups such as phenyl and N-alkane ligands including methyl, ethyl, propyl, butyl, pentyl, hexyl, heptyl and octyl (Queiroz et al, supra). Many types of HIC columns are available commercially. These include, but are not limited to, SEPHAROSE™ columns such as Phenyl SEPHAROSE™ (Pharmacia LCK Biotechnology, AB, Sweden), FAST FLOW™ column with low or high substitution (Pharmacia LKB Biotechnology, AB, Sweden); Octyl SEPHAROSE™ High Performance column (Pharmacia LKB Biotechnology, AB, Sweden); FRACTOGEL™ EMD Propyl or FRACTOGEL™, EMD Phenyl columns (E. Merck, Germany); MACRO-PREP™ Methyl or MACRO-PREP™ t-Butyl Supports (Bio-Rad, California); WP HI-Propyl ($C_3$)™ column (J. T. Baker, New Jersey); and TOYOPEARL™ ether, phenyl or butyl columns (TosoHaas, Pennsylvania).

In one embodiment, TOYOPEARL™ BUTYL-M columns have been used for purifying proteins as described in Examples 1 and 2.

The mobile phase of HIC according to the present invention is the two salt solution. Commercial applications processes for purifying large quantities of proteins require that the exact ion concentrations of the two salt solution be constant and consistent. Therefore, the adjustment of the dissolved salt solution is made with the acid form of the salt, such as citric acid mixed with citrate to get an exact ion concentration. The salts of the present invention are all commercially available from a number of vendors. At least one salt in the two salt solution will have a buffering effect at the pH at which the protein to be purified is stable. In one embodiment, the buffering capacity of at least one salt is between pH 5 to about pH 7 according to the present invention.

The protocol for using an HIC column according to the present invention is generally as follows. The column is first regenerated with several column volumes of sodium hydroxide, 0.5 N NaOH, for example, then washed with water. The column is then equilibrated with several column volumes of equilibration buffer, which is the same buffer containing the protein preparation for loading onto the column. The protein preparation is prepared by "conditioning" or mixing with the two salt buffered solution. Generally the salt solution is added slowly with the protein preparation at a rate of about 1-2% volume per minute, to avoid protein destabilization. Next, the protein/buffered salt solution mixture is loaded onto the column, and the column washed with several column volumes of equilibrium buffer. The HIC column is then eluted. Elution can preferably be accomplished by decreasing the salt concentration of the buffer using a salt gradient or isocratic elution. The gradient or step starts at equilibrium buffer salt concentration, and is then reduced as a continuous gradient, or as discrete steps of successively lower concentrations. The elution generally concludes with washing the column with a solution such as a no-salt buffer, such as low ionic strength MES buffer, for example. Elution of the subject protein can also be accomplished by changing the polarity of the solvent, and by adding detergents to the buffer. The protein when purified can be diafiltered or diluted to remove any remaining excess salts.

The method of purifying a protein according to the present invention applies to protein preparations at any stage of purification. Protein purification of recombinantly produced proteins typically includes filtration and/or differential centrifugation to remove cell debris and subcellular fragments, followed by separation using a combination of different chromatography techniques.

A wide range of concentrations of protein can be loaded onto an HIC column using the two salt system of the present invention. The protein preparation to be purified according to the present invention may be of any concentration, however preferably may be varied from about 0.1 mg/ml to about 100 mg/ml or more, more preferably between about 2.5 mg/ml to about 20 mg/ml in an aqueous solution. As used herein the term "protein" is used interchangeably with the term "polypeptide" and is considered to be any chain of at least ten amino acids or more linked by peptide bonds. As used herein, the term "protein preparation" refers to protein in any stage of purification in an aqueous solution. The concentration of a protein preparation at any stage of purification can be determined by any suitable method. Such methods are well known in the art and include: 1) colorimetric methods such as the Lowry assay, the Bradford assay, and the colloidal gold assay; 2) methods utilizing the UV absorption properties of proteins; and 3) visual estimation based on stained protein bands in gels relying on comparison with protein standards of known quantity on the same gel such as silver staining. See, for example, Stoschek *Methods in Enzymol.* 182:50-68 (1990).

For the purposes of the present invention a protein is "substantially similar" to another protein if they are at least 80%, preferably at least about 90%, more preferably at least about 95% identical to each other in amino acid sequence, and maintain or alter the biological activity of the unaltered protein. Amino acid substitutions which are conservative substitutions unlikely to affect biological activity are considered identical for the purposes of this invention and include the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and the reverse. (See, for example, Neurath et al., *The Proteins*, Academic Press, New York (1979)).

The method of purifying proteins according to the present invention is directed to all types of proteins. The present invention is particularly suitable for purifying protein-based drugs, also known as biologics. Typically biologics are produced recombinantly, using procaryotic or eukaryotic expression systems such as mammalian cells or yeasts, for example. Recombinant production refers to the production of the desired protein by transformed host cell cultures containing a vector capable of expressing the desired protein. Methods and vectors for creating cells or cell lines capable of expressing recombinant proteins are described for example, in Ausabel et al, eds. *Current Protocols in Molecular Biology*, (Wiley & Sons, New York, 1988, and quarterly updates).

The method of purifying proteins according to the present invention is particularly applicable to antibodies. As used herein, the term "antibody" refers to intact antibodies including polyclonal antibodies (see, for example *Antibodies: A Laboratory Manual*, Harlow and Lane (eds), Cold Spring Harbor Press, (1988)), and monoclonal antibodies (see, for example, U.S. Pat. Nos. RE 32,011, 4,902,614, 4,543,439, and 4,411,993, and *Monoclonal Antibodies: A New Dimension in Biological Analysis*, Plenum Press, Kennett, McKearn and Bechtol (eds.) (1980)). As used herein, the term "antibody" also refers to a fragment of an antibody such as F(ab), F(ab'), F(ab')$_2$, Fv, Fc, and single chain antibodies which are produced by recombinant DNA techniques or by enzymatic or chemical cleavage of intact antibodies. The term "antibody" also refers to bispecific or bifunctional antibodies, which are an artificial hybrid antibody having two different heavy/light chain pairs and two different binding sites. Bispecific antibodies can be produced by a variety of methods including fusion of hybridomas or linking of Fab' fragments. (See Songsivilai et al, *Clin. Exp. Immunol.* 79:315-321 (1990), Kostelny et al., *J. Immunol.* 148:1547-1553 (1992)). As used herein the term "antibody" also refers to chimeric antibodies, that is, antibodies having a human constant antibody immunoglobin domain is coupled to one or more non-human variable antibody immunoglobin domain, or fragments thereof (see, for example, U.S. Pat. No. 5,595,898 and U.S. Pat. No. 5,693,493). Antibodies also refers to "humanized" antibodies (see, for example, U.S. Pat. No. 4,816,567 and WO 94/10332), minibodies (WO 94/09817), and antibodies produced by transgenic animals, in which a transgenic animal containing a proportion of the human antibody producing genes but deficient in the production of endogenous antibodies are capable of producing human antibodies (see, for example, Mendez et al., *Nature Genetics* 15:146-156 (1997), and U.S. Pat. No. 6,300,129). The term "antibodies" also includes multimeric antibodies, or a higher order complex of proteins such as heterdimeric antibodies. "Antibodies" also includes anti-idiotypic antibodies including anti-idiotypic antibodies against an antibody targeted to the tumor antigen gp72; an antibody against the ganglioside GD3; or an antibody against the ganglioside GD2.

One exemplary antibody capable of being purified according to the present invention is an antibody that recognizes the epidermal growth factor receptor (EGFR), referred to as "an antibody against EGFR" or an "anti-EGFR antibody", described in U.S. Pat. No. 6,235,883, which is herein incorporated by reference in its entirety. An antibody against EGFR includes but is not limited to all variations of the antibody as described in U.S. Pat. No. 6,235,883. Many other antibodies against EGFR are well known in the art, and additional antibodies can be generated through known and yet to be discovered means. A preferred antibody against EGFR is a fully human monoclonal antibody capable of inhibiting the binding of EGF to the EGF receptor. The purification of an antibody against EGFR using a dual salt HIC according to the present invention is described herein in Example 1.

Additional exemplary proteins are three IgG monoclonal antibodies having the following designations: mAb1, mAb2, and mAb3. Purification of these monoclonal antibodies according to the present invention is described herein in Example 2.

The invention is also particularly applicable to proteins, in particular fusion proteins, containing one or more constant antibody immunoglobin domains, preferably an Fc domain of an antibody. The "Fc domain" refers to the portion of the antibody that is responsible for binding to antibody receptors on cells. An Fc domain can contain one, two or all of the following: the constant heavy 1 domain ($C_H1$), the constant heavy 2 domain ($C_H2$), the constant heavy 3 domain ($C_H3$), and the hinge region. The Fc domain of the human IgG1, for example, contains the $C_H2$ domain, and the $C_H3$ domain and hinge region, but not the $C_H1$ domain. See, for example, C. A. Hasemann and J. Donald Capra, Immunoglobins: Structure and Function, in William E. Paul, ed. *Fundamental Immunology*, Second Edition, 209, 210-218 (1989). As used herein the term "fusion protein" refers to a fusion of all or part of at least two proteins made using recombinant DNA technology or by other means known in the art.

An example of an Fc-containing protein capable of being purified according to the present invention is tumor necrosis factor receptor-Fc fusion protein (TNFR:Fc). As used herein the term "TNFR" (tumor necrosis factor receptor) refers to a protein having an amino acid sequence that is identical or substantially similar to the sequence of a native mammalian tumor necrosis factor receptor, or a fragment thereof, such as the extracellular domain. Biological activity for the purpose of determining substantial similarity is the capacity to bind tumor necrosis factor (TNF), to transduce a biological signal initiated by TNF binding to a cell, and/or to cross-react with anti-TNFR antibodies raised against TNFR. A TNFR may be any mammalian TNRF, including murine and human, and are described in U.S. Pat. No. 5,395,760, U.S. Pat. No. 5,945,397, and U.S. Pat. No. 6,201,105, all of which are herein incorporated by reference. TNFR:Fc is a fusion protein having all or a part of an extracellular domain of any of the TNFR polypeptides including the human p55 and p75 TNFR fused to an Fc region of an antibody. An exemplary TNFR:Fc is a dimeric fusion protein made of the extracellular ligand-binding portion of the human 75 kDa tumor necrosis factor receptor linked to the Fc portion of the human IgG1 from natural (non-recombinant) sources. The purification of the exemplary TNFR:Fc according to the present invention is described in Example 2 below.

Additional proteins capable of being purified according to the present invention include differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand.

An exemplary ligand capable of being purified according to the present invention is a CD40 ligand (CD40L). The native mammalian CD40 ligand is a cytokine and type II membrane polypeptide, having soluble forms containing the extracellular region of CD40L or a fragment of it. As used herein, the term "CD40L" refers to a protein having an amino acid sequence that is identical or substantially similar to the sequence of a native mammalian CD40 ligand or a fragment thereof, such as the extracellular region. As used herein, the term "CD40 ligand" refers to any mammalian CD40 ligand including murine and human forms, as described in U.S. Pat. No. 6,087,329, which is herein incorporated by reference in its entirety. Biological activity for the purpose of determining substantial similarity is the ability to bind a CD40 receptor. A preferred embodiment of a human soluble CD40L is a trimeric CD40L fusion protein having a 33 amino acid oligomerizing zipper (or "leucine zipper") in addition to an extracellular region of human CD40L as described in U.S. Pat. No. 6,087,329. The 33 amino acid sequence trimerizes spontaneously in solution.

In addition, a number of other proteins are capable of purified according to the improved purification methods of the present invention include a number of proteins of commercial, economic, pharmacologic, diagnostic, or therapeutic value. Such proteins may be monomeric or multimeric. These proteins include, but are not limited to, a protein or portion of a protein identical to, or substantially similar to, one of the following proteins: a flt3 ligand, erythropoietin, thrombopoietin, calcitonin, Fas ligand, ligand for receptor activator of NF-kappa B (RANKL), TNF-related apoptosis-inducing ligand (TRAIL), thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor, leukemia inhibitory factor, oncostatin-M, and various ligands for cell surface molecules ELK and Hek (such as the ligands for eph-related kinases or LERKS). Descriptions of proteins that can be stabilized according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991).

Additional proteins capable of being purified according to the present invention are receptors for any of the above-mentioned proteins or proteins substantially similar to such receptors or a fragment thereof such as the extracellular domains of such receptors. These receptors include, in addition to both forms of tumor necrosis factor receptor (referred to as p55 and p75) already described: interleukin-1 receptors (type 1 and 2), interleukin-4 receptor, interleukin-15 receptor, interleukin-17 receptor, interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or apoptosis-inducing receptor (AIR). Proteins of interest also includes antibodies which bind to any of these receptors.

Proteins of interest capable of being purified according to the present invention also include enzymatically active proteins or their ligands. Examples include polypeptides which are identical or substantially similar to the following proteins or portions of the following proteins or their ligands: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands. Proteins of interest also include antibodies that bind to the above-mentioned enzymatically active proteins or their ligands.

Additional proteins of interest capable of being purified according to the present invention are conjugates having an antibody and a cytotoxic or luminescent substance. Such substances include: maytansine derivatives (such as DM1); enterotoxins (such as a *Staphlyococcal* enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6). Examples of antibodies or antibody/cytotoxin or antibody/luminophore conjugates contemplated by the invention include those that recognize the following antigens: CD2, CD3, CD4, CD8, CD11a, CD14, CD18, CD20, CD22, CD23, CD25, CD33, CD40, CD44, CD52, CD80 (B7.1), CD86 (B7.2), CD 147, IL-4, IL-5, IL-8, IL-10, IL-2 receptor, IL-6 receptor, PDGF-$\beta$, VEGF, TGF, TGF-$\beta$2, TGF-$\beta$1, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TNF-$\alpha$, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-$\gamma$-1 receptor, HLA-DR 10 beta, HLA-DR antigen, L-selectin, IFN-$\gamma$, Respiratory Syncitial Virus, human immunodeficiency virus (HIV), hepatitis B virus (HBV), *Streptococcus mutans*, and *Staphylococcus aureus*.

The present invention is particularly useful in the context of commercial production and purification of proteins, especially recombinantly produced proteins. By increasing the capacity of one step in the overall purification scheme of a commercially important protein, the present invention can reduce the number of cycles required to purify a batch of protein. The present invention therefore increases the efficiency of protein purification, without reducing the quality of the protein product. For large-scale production of commercially important biologics, for example, this represents a significant savings in cost and time.

The invention having been described, the following examples are offered by way of illustration, and not limitation.

Example I

Various combinations of salt solutions were tested for their ability to increase the dynamic capacity of an HIC column used for purifying an antibody against epidermal growth factor receptor (antibody against EGFR).

First the range of effective concentrations for single salts ("salts") and two salt buffers for the antibody against EGFR was determined by plotting precipitation curves for single salts and their combinations. The following salts were used: sodium citrate, sodium phosphate, sodium acetate, and sodium phosphate. All buffers were made by weighing out the appropriate chemicals, dissolving at approximately 80% of the final volume, and adjusting the pH using 11.2 N HCl or 10 N NaOH to pH 6.0, at room temperature (21-23° C.), and bringing up to volume. For commercial applications, however, the buffered salts are prepared by mixing a salt with its acid form, such as sodium citrate with citric acid, to achieve an exact ion concentration, rather than adjusting to a pH with other acids or bases.

Figure 1B:
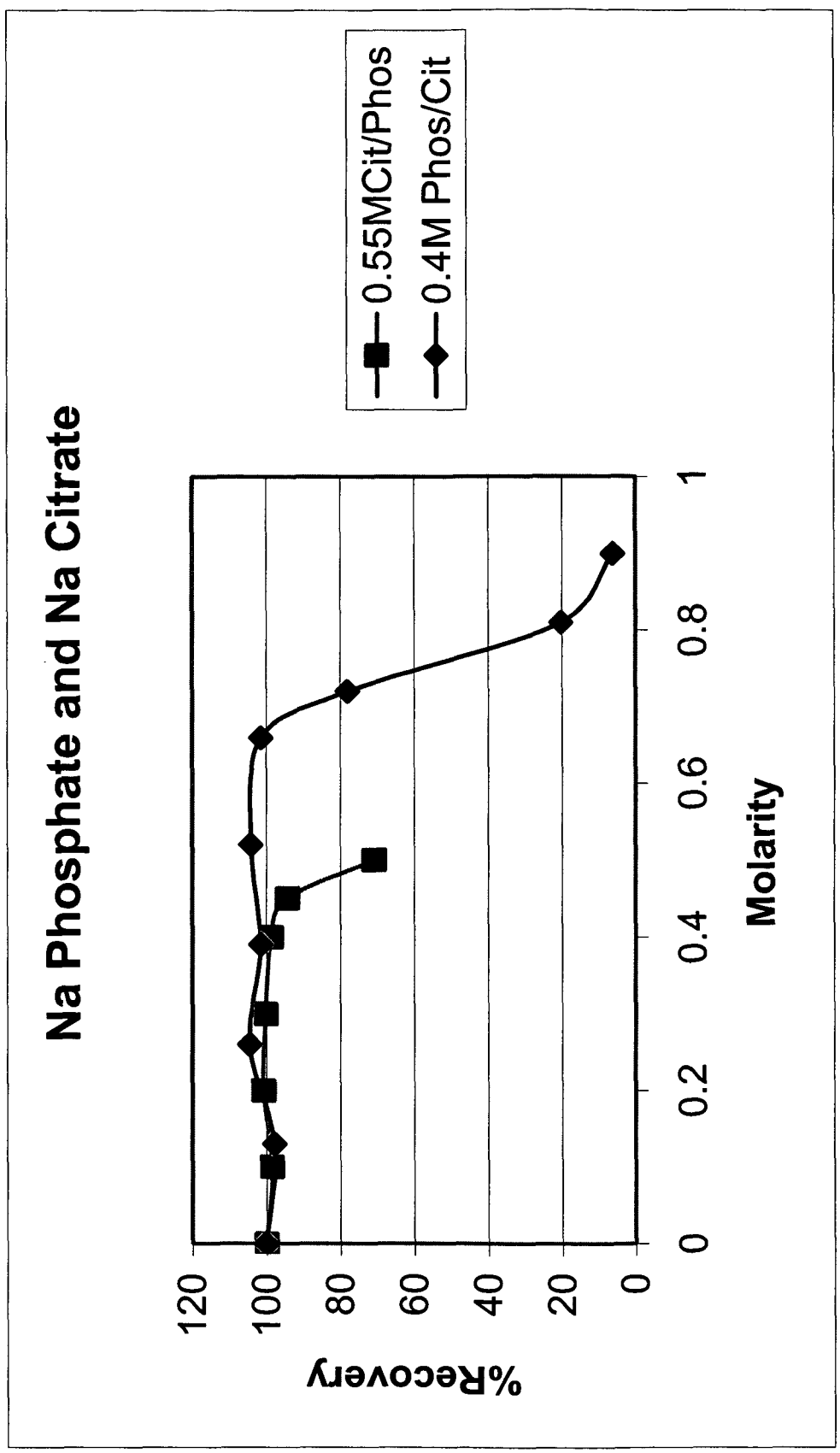
FIG. 1B shows the precipitation curves for 0.55 M sodium citrate with increasing concentrations of sodium phosphate, and 0.4 M sodium phosphate with increasing concentrations of sodium citrate.
Figure 1C:
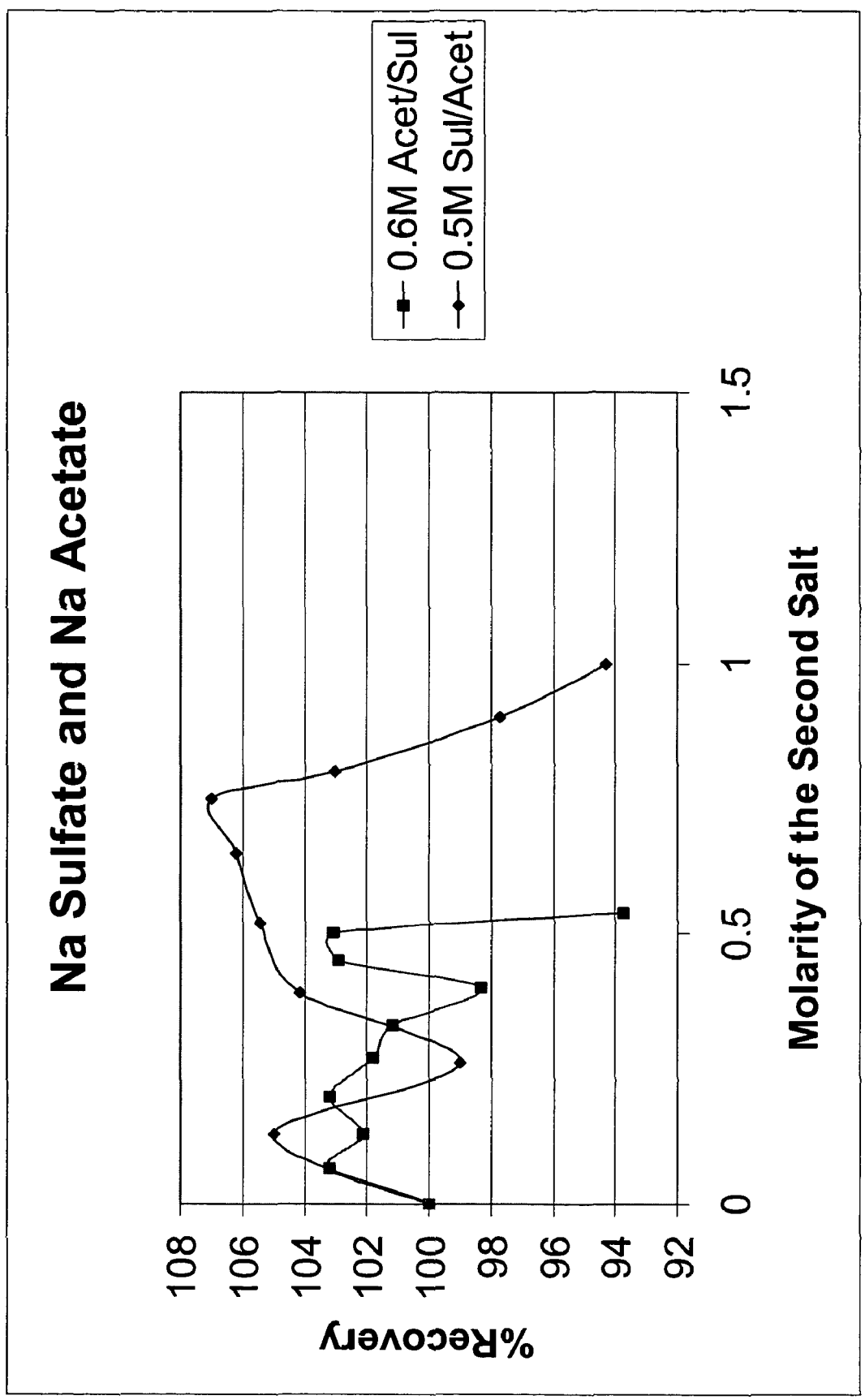
FIG. 1C shows the precipitation curves for 0.6 M sodium acetate with increasing concentrations of sodium sulfate, and 0.5 M sodium phosphate with increasing concentrations of sodium sulfate.
Figure 1D:
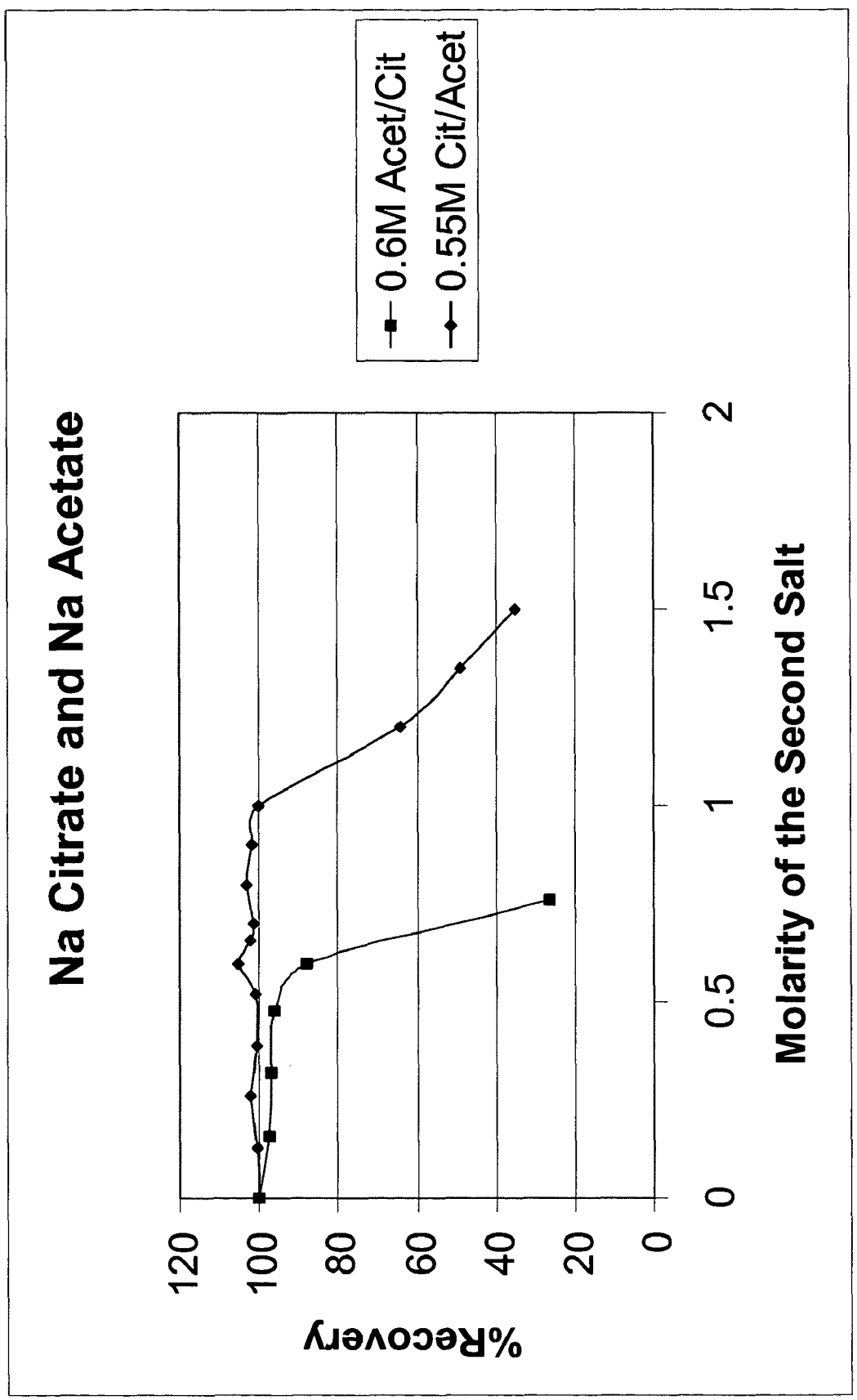
FIG. 1D shows the precipitation curves for 0.6 M sodium acetate with increasing concentrations of sodium citrate, and 0.55 M sodium citrate with increasing concentrations of sodium acetate.
Figure 1E:
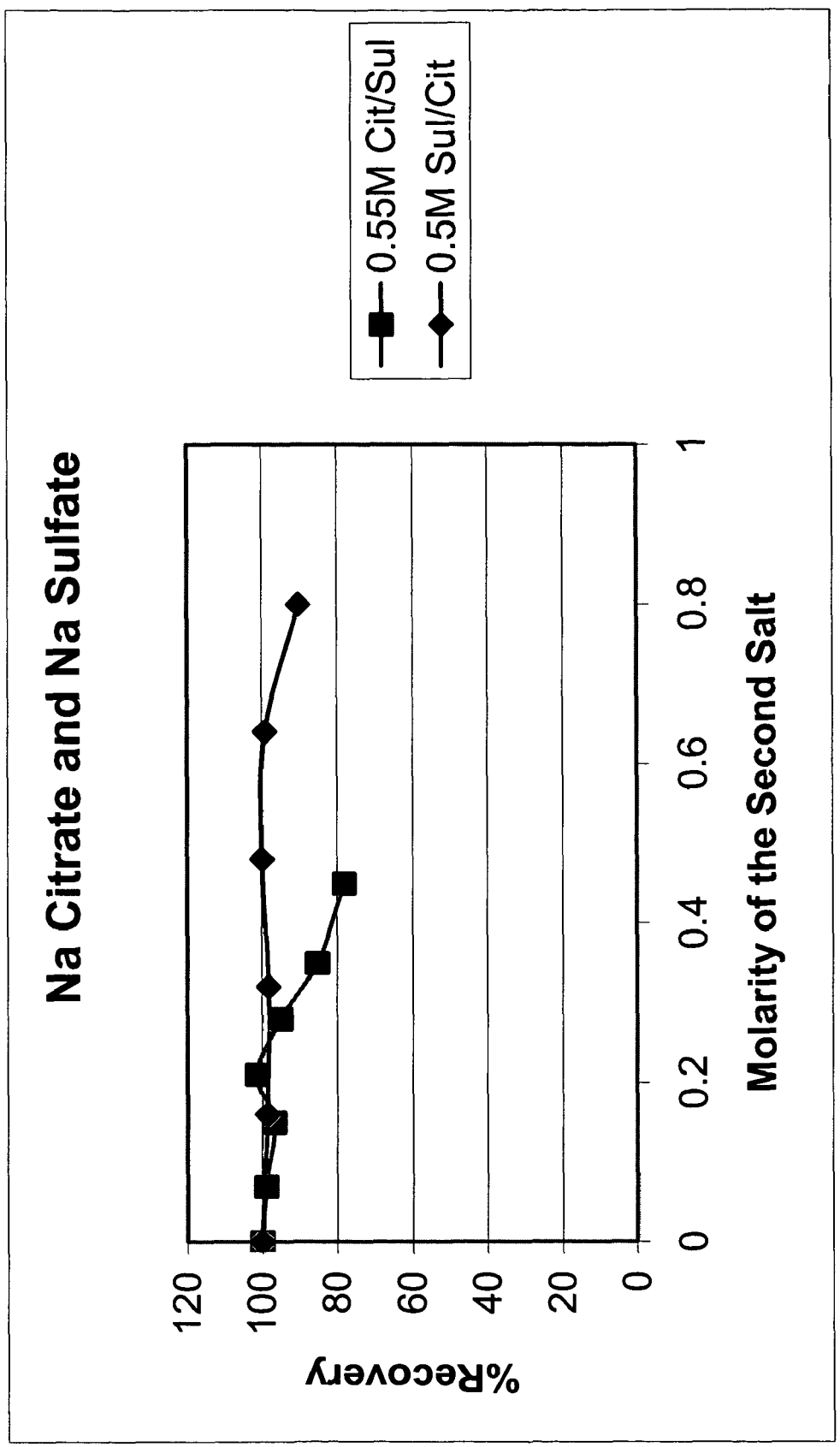
FIG. 1E shows the precipitation curves for 0.55 M sodium citrate with increasing concentrations of sodium sulfate, and 0.5 M sodium sulfate with increasing concentrations of sodium citrate.

The antibody preparation used for testing was a partially purified eluant from a previous column having a concentration of approximately 5 mg/ml protein. Precipitation studies of this antibody using individual buffers were performed as follows: the antibody preparation was mixed with the buffer stock to make between 0 and 1.2 M final concentration of salt. The samples incubated for 20 minutes, centrifuged for 10 minutes at approximately 6000×g, filtered, and the supernatant assayed for protein. The control sample was diluted with water, and its supernatant reading was taken as 100% recovery. A salting out or precipitation curve was generated for the antibody by plotting amount of protein in the supernatant (percent recovery, compared with the control) versus salt molarity. The percent recovery decreased significantly at greater than about 0.6 M for sodium citrate, while the percent recovery decreased significantly at greater than about 0.8 M for sodium phosphate buffer, at greater than about 1.2 M for sodium acetate, and at greater than about 0.6 M for sodium sulfate. Using this information, a second series of salting out curves for two salt combinations was generated in which the concentration of the first salt was kept constant, while the concentration of the second salt was increased. The precipitation curves were generated by incubating the antibody and two salt mixture for twenty minutes and centrifuging as described for the single salts solutions. For example, sodium citrate was kept at 0.55 M while the concentration of sodium phosphate was increased, and the percent recovery of the antibody in the supernatant was measured and compared with that of the control. The reverse test was also performed keeping 0.4 M sodium phosphate constant while varying the concentration of sodium sulfate. The results are shown in FIG. 1A through E. These results show that reduced concentrations of the salts together compared with a salt alone could precipitate the protein. This indicated that reduced concentrations of each salt in combination produced equivalent hydrophobic effects compared with higher concentrations of each salt alone.

The results of the single and two salt precipitations provided a range of single and combined salt concentrations for the determination of dynamic capacity for an HIC column for the antibody against EGFR. The dynamic capacity was determined according to the following protocol. An approximately 5 mg/ml antibody preparation was "conditioned" by diluting 1:1 with the appropriate buffered salt stock solution (2×). The salt stock was added to the antibody preparation at a rate of 1-2% volume per minute with stirring. Further salt dilution was performed as necessary to provide a range of salt concentrations, and the mixture of antibody preparation and salt buffer was filtered on a 0.2 um cellulose filter. This mixture was the hydrophobic interaction chromatography (HIC) load. The HIC column used to determine dynamic capacity for single and two salt combinations was a Millipore (Bellerica, Mass.) VANTAGE column having 1.1 cm diameter and packed to 8.5 mL column volume (CV) (9 cm bed height) with TOYOPEARL™ BUTYL 650 M resin (TosoHaas). The column was prepared by regenerating with 0.5N sodium hydroxide at 180 cm/hr for 3 column volumes (CV), washing for 3 CV at 180 cm/hr with water, then equilibrating the column at 180 cm/hr with the appropriate salt buffer or salt combination. Then the load mixture was loaded at 90 cm/hr and washed at 90 cm/hr with 3 CV of the same salt buffer (equilibrium buffer). For determining dynamic capacity, the columns were overloaded with protein, so that fractions were collected during the loading ("flow-through") and washing steps. Protein content was determined by absorption at 280 nm, or by SDS-PAGE gels. The load concentration in mg/ml-resin at which the % breakthrough is zero is considered to be the dynamic capacity of the antibody at that salt concentration. The dynamic capacity was determined from plotting HIC load versus percent breakthrough (BT) (flow-through concentration/load concentration).

The antibody was then eluted at 180 cm/hr using a step elution or step gradient starting with the equilibrium conditions to a concentration of 0.2 M salt. Fractions were collected and SDS-PAGE analysis was performed on 4-20% Tris/Glycine Novex gels using silver stain (Pharmacia One-Plus™ kit) to visualize protein bands.

Two salt concentrations were optionally further modified in order to stabilize the monomer antibody preparation at room temperature, rather than 4-8° C., and also to minimize the formation of aggregates in the antibody sample. For example, the dynamic capacity of the column for the antibody using 0.4 M sodium phosphate buffer was 43/ml-r (ml-resin); the dynamic capacity of 0.35 M sodium phosphate was 40 mg/ml-r, and the dynamic capacity of 0.3 M sodium phosphate was 38 mg/ml-r. However, 25% protein loss was found to occur at 0.5 M phosphate at room temperature, while only 8% loss was found in 0.4 M for up to six days at room temperature. In addition, it was found that material that precipitated out between 0.3M and 0.4 M salt concentrations included almost all of the high molecular weight aggregates (HMW).

In addition, the rate at which the salt stock was mixed with the antibody preparation influenced the stability of the antibody. At a rate of 2% volume/minute, only about 2% of the antibody was lost as fragments of the monomer, as opposed to 12% lost at 10% volume/minute.

The dynamic capacities of the HIC column for the antibody against EGFR for the various single and combination salts were determined as described above and are shown in Table 1 below.

TABLE 1

Dynamic capacities of antibody against EGFR with four salts and their combinations. Only anions are listed; the cations were sodium for every salt

| Experimental Conditions | Dynamic Capacity (mg/ml-r) |
| --- | --- |
| 0.55M Citrate | 24 |
| 0.5M Phosphate | 12 |
| 0.8M Sulfate | 24 |
| 1.2 M Acetate | 5 |
| 0.55M Citrate/0.3M Sulfate | 30 |
| 0.6M Acetate/0.5M Citrate | 29 |
| 0.35M Phosphate/0.6M Citrate | 39 |
| 0.6M Acetate/0.7M Sulfate | 27 |
| 0.5M Citrate/1M Acetate | 34 |
| 0.5M Sulfate/1M Acetate | 33 |
| 0.4M Phosphate/0.3M Sulfate | 15 |
| 0.5M Sulfate/0.3M Citrate | 33 |
| 0.5M Sulfate/0.3M Phosphate | 17 |
| 0.3M Citrate/0.6M Phosphate | 35 |

Table 1 shows that the combinations of citrate/sulfate, acetate/citrate, phosphate/citrate, acetate/sulfate, citrate/acetate, sulfate/acetate, sulfate/citrate, and citrate/phosphate increased the dynamic capacity of the HIC column for the antibody by factors varying from approximately 1.5 to 2 times or more that of each salt alone. The phosphate/sulfate combination did not increase the dynamic capacity for the following reasons: sulfate in combination with phosphate resulted in a precipitate, so that lower concentrations of sulfate were required to prevent precipitation. These low concentrations proved too low to improve dynamic capacity. In addition, phosphate and acetate did not prove to be an effective combination due to the precipitation which resulted when the two salts were mixed.

Example 2

Using the same procedures as described in Example 1 the dynamic capacities of four additional proteins was determined for the single salts sodium phosphate and sodium citrate, and two salt combination 0.55 M sodium citrate with phosphate concentration varied. The additional proteins were the fusion protein TNFR:Fc described above, and three monoclonal antibodies designated mAb1, mAb2, and mAb3. The three monoclonal antibodies were partially purified and obtained as eluants from other types of chromatography columns. The TNFR:Fc fusion protein was obtained as a fully purified protein. The concentrations of the proteins used was between 4-5 mg/ml, for this particular experiment.

The precipitation curves for sodium citrate and sodium phosphate alone were first determined for each protein, and then a two salt precipitation curve for 0.55M sodium citrate with sodium phosphate varied was determined. The concentration at which each protein begins to precipitate is given in Table 2 below.

TABLE 2

Salt concentrations at which protein begins to precipitate (taken from the precipitation curves.)

| Protein | Conc. Sodium Citrate | Conc. Sodium Phosphate | Combination Salt |
| --- | --- | --- | --- |
| mAb1 | 0.6M | 0.9M | 0.55M NaCitrate/ 0.4M Na Phosphate |
| mAb2 | 0.7M | 1.1M | 0.55M Na Citrate/ 0.4M Na Phosphate |
| mAb3 | 0.7M | 1.0 M | 0.55M Na Citrate/ 0.2M Na Phosphate |
| TNFR:Fc | 0.55M | 1.0 M | 0.4M Na Citrate/ 0.2M Na Phosphate |

It is clear from Table 2 that the combination of salts precipitated the proteins at lower concentrations compared to the concentrations of each salt alone.

The dynamic capacities of these proteins on TOYOPEARL™ BUTYL 650M (TosoHaas) gels was determined for the salt concentrations shown in Table 2, using the same procedure described above for the antibody against EGFR. The results are given in Table 3 below.

TABLE 3

Dynamic capacities under the salt conditions listed in Table 2.

| Protein | Na Citrate | Na Phosphate | Combination |
| --- | --- | --- | --- |
| mAb1 | 37 | 20 | 49 |
| mAb2 | 36 | 30 | 44 |
| mAb3 | 21 | 12 | 25 |
| TNFR:Fc | 17 | 18 | 25 |

Again, it is clear that the combination of salts increased the dynamic capacity for all four proteins over that achieved using the single salts by 1.5 to 2 times.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A process for purifying a protein on a hydrophobic interaction chromatography column such that the dynamic capacity of the column is increased for that protein comprising mixing a preparation containing the protein with a combination of a first salt and a second salt, loading the mixture onto a hydrophobic interaction chromatography column, and eluting the protein, wherein the first and second salts are citrate and phosphate salts, and wherein the concentration of each of the first salt and the second salt in the mixture is between about 0.1 M and about 1.0.

2. The process of claim 1 wherein the pH of the mixture loaded onto the column is between about pH 5 and about pH 7.

3. The process of claim 1 wherein the column is eluted with a solution having a pH between about pH 5 and about pH 7.

4. The process of claim 1 wherein the citrate and phosphate salts are selected from the group consisting of sodium, potassium and ammonium salts.

5. The process of claim 1 wherein the protein is a fusion protein or an antibody.

6. The process of claim 1, further comprising diluting the protein.

7. The process of claim 1, further comprising filtering the protein.

8. The process of claim 1, further comprising formulating the protein.

9. The process of claim 1, further comprising lyophilizing the protein.

10. A process of increasing the dynamic capacity of a hydrophobic interaction chromatography column for a particular protein, comprising mixing a preparation containing the protein with a combination of a first salt and a second salt, and loading the mixture onto a hydrophobic interaction chromatography column, wherein the first and second salts are citrate and phosphate salts, and wherein the concentration of each of the first and second salts in the mixture is between about 0.1M and about 1.0 M.

11. The process of claim 10 wherein the pH of the mixture loaded onto the column is between about pH 5 and about pH 7.

12. The process of claim 10, wherein the citrate and phosphate salts are selected from the group consisting of sodium, potassium and ammonium salts.

13. The process of claim 10 wherein the protein is a fusion protein or an antibody.

* * * * *

UNITED STATES PATENT AND TRADEMARK OFFICE
CERTIFICATE OF CORRECTION

PATENT NO. : 7,781,395 B2  
APPLICATION NO. : 10/895581  
DATED : August 24, 2010  
INVENTOR(S) : Anna Senczuk et al.

Page 1 of 1

It is certified that error appears in the above-identified patent and that said Letters Patent is hereby corrected as shown below:

Title page item (73)

The Assignee for the above-referenced Patent is:
AMGEN INC., Thousand Oaks, California Signed and Sealed this
Twenty-second Day of February, 2011

David J. Kappos
*Director of the United States Patent and Trademark Office*